United States Patent [19]
Scherl et al.

[11] Patent Number: 5,610,072
[45] Date of Patent: Mar. 11, 1997

[54] DETECTION OF CAFFEINE IN BEVERAGES

[76] Inventors: Michael Scherl, 257 N. Woodland St., Englewood, N.J. 07631; Zev Scherl, 88 Pine Crest Rd., Orange, Conn. 06477; Susan B. Fiedler, 200 Hemlock Rd., New Haven, Conn. 06515

[21] Appl. No.: 620,545

[22] Filed: Mar. 25, 1996

[51] Int. Cl.$^6$ .......................... G01N 33/00; G01N 33/02
[52] U.S. Cl. ................... 436/96; 436/98; 422/56; 422/61
[58] Field of Search ................... 422/56, 61, 58; 436/96, 98

[56] References Cited

U.S. PATENT DOCUMENTS

| | | | |
|---|---|---|---|
| 3,598,995 | 8/1971 | Inoue et al. | 250/71 R |
| 4,281,061 | 7/1981 | Zuk et al. | 436/800 |
| 4,362,697 | 12/1982 | Tabb et al. | 422/56 |
| 4,868,106 | 9/1989 | Ito et al. | 422/56 |

*Primary Examiner*—Lyle A. Alexander
*Attorney, Agent, or Firm*—William W. Jones

[57] ABSTRACT

The caffeine content of a beverage is measured by inserting a dipstick into the beverage. The dipstick is impregnated with a reagent that changes color when reacted with caffeine. The degree of color change will be proportional to the concentration of caffeine in the beverage. The dipstick may be provided with a graded color chart which can be compared to the color of the dipstick so as to ascertain the concentration of caffeine in the beverage. The dipstick will preferably include a beverage dipping section; an adjacent temperature moderation section; and an adjacent reagent-impregnated section. The beverage is preferably wicked from its container to the reagent-impregnated section of the dipstick. In this manner, the reagent is never directly admixed with the beverage in the container.

11 Claims, 1 Drawing Sheet

DETECTION OF CAFFEINE IN BEVERAGES

TECHNICAL FIELD

This invention relates to the detection of caffeine in a beverage. More particularly, this invention relates to a method and device for detecting the concentration of caffeine in a beverage which can be used by a consumer of the beverage at the time of consumption.

BACKGROUND ART

Caffeine is a bitter crystalline alkaloid. There are a variety of biological effects and symptoms caused by the ingestion of caffeine including tachycardia, diuresis, headaches, decrease in fine motor coordination, insomnia, and central neurological stimulation.

Caffeine is the active ingredient in a variety of beverages. These beverages include, but are not limited to: coffee, tea, soda, hot chocolate, and the like. These beverages are often sold in caffeinated and decaffeinated formulations.

As evidenced by the huge decaffeinated market, the caffeine content of a beverage significantly effects purchase intent and consumption for many people. Tea and coffee are commonly consumed at the conclusion of the evening meal. It is during, but not limited to, the evening hours when many people try to avoid the stimulating effects of caffeine. Pregnant women may not drink any caffeinated beverages for fear of a teratogenic effect. Both men and women avoid caffeinated beverages because caffeine is a known diuretic. Also, as people age, they become increasingly sensitive to the effects of caffeine.

Often these beverages are served in a container that does not verify the presence or absence of caffeine, or the concentration of caffeine in the beverage. Coffee drinkers may be concerned that the content of caffeine indicated by the manufacturer is not accurate, and therefore, they may abstain from coffee in order to avoid any chance of ingesting caffeine.

It would be desirable to provide a methodology which would enable a consumer or a server of an allegedly decaffeinated beverage to quickly and easily determine the concentration of caffeine in the beverage.

DISCLOSURE OF THE INVENTION

This invention relates to a method and device for measuring the concentration of caffeine in a beverage. The device preferably consists of a dry reagent test strip in the form of a dipstick which can be dipped into the beverage in question and then observed for any color change in a reagent-impregnated section of the dipstick. The dipstick will preferably be formed with three adjacent sections. The first section is a dip section which is the part of the device which is dipped into the beverage being tested. The dip section will preferably be formed from an absorbent material such as paper or nylon, and will form one end of the dipstick. Adjacent to the dip section will be a temperature moderation section that is formed from a liquid wicking material such as paper or nylon. The purpose of this section is to moderate the temperature of the beverage being tested so that if the beverage is a hot beverage, it will cool as it passes through the moderation section; and if the beverage is a cold beverage, it will warm as it passes through the moderation section. The final section of the dipstick is the reagent section which is located on the end of the dipstick opposite the dip section. The reagent section contains the reagents used to detect the concentration of caffeine in the beverage. The reagent section preferably includes a liquid-absorbent, reagent-impregnated core which is covered by a transparent gas-permeable plastic skin. The skin protects the user against exposure to the reagents while at the same time allowing oxygen-dependent chemical reactions to take place in the reagent section. By reason of its physical construction, the dipstick can be used to analyze both hot and cold beverages for caffeine content, and will ensure that the reagents in the dipstick will not be contacted by the user. Additionally, the reagents in the dipstick cannot leak into the beverage container from the dipstick.

It is therefore an object of this invention to provide a convenient method and device for testing a beverage for the presence of caffeine.

It is a further object of this invention to provide a method and device of the character described which enables the detection of the concentration of caffeine in a beverage that one is about to consume.

It is another object of this invention to provide a method and device of the character described which involves the production of a characteristic color in the presence of caffeine.

It is an additional object of this invention to provide a method and device of the character described which is useful for testing both hot and cold beverages for the presence of caffeine.

These and other objects and advantages of the invention will become more readily apparent from the following detailed description of an embodiment of the invention when taken in conjunction with the accompanying drawings, in which:

DETAILED DESCRIPTION OF THE INVENTION

Figure 1:
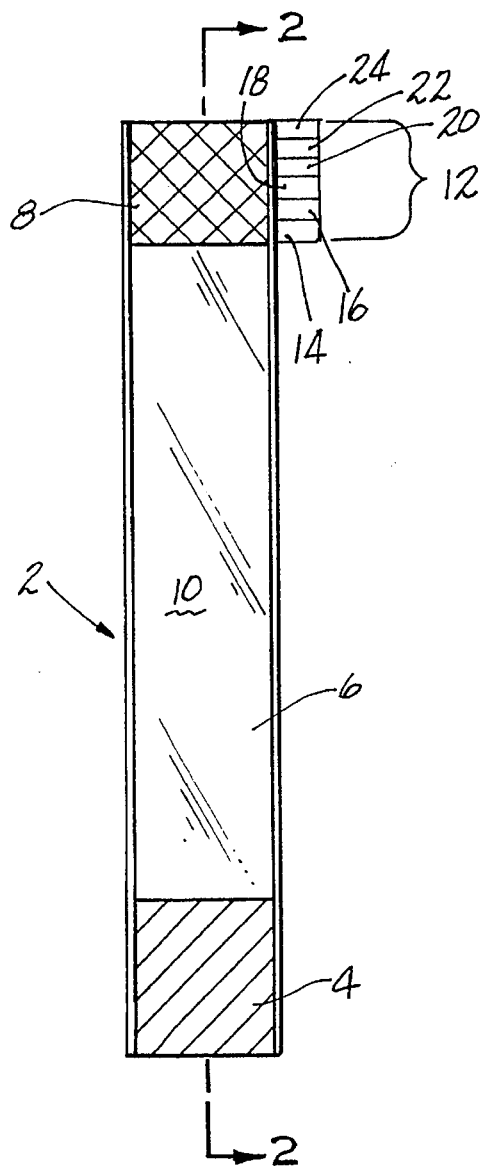
FIG. 1 is an elevational view of a dipstick which can be used to test a beverage for caffeine content in accordance with this invention.
Figure 2:
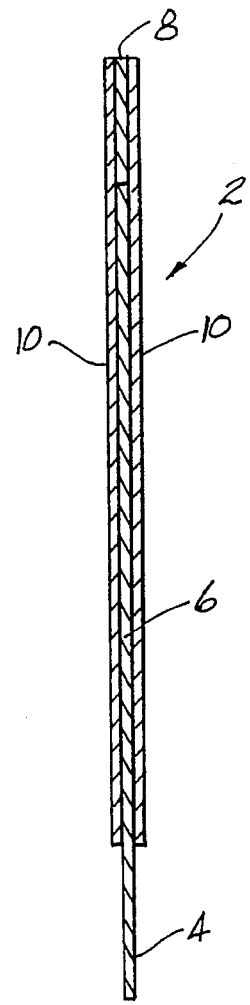
FIG. 2 is a cross-sectional view of the dipstick taken along line 2—2 of FIG. 1.
Figure 3:
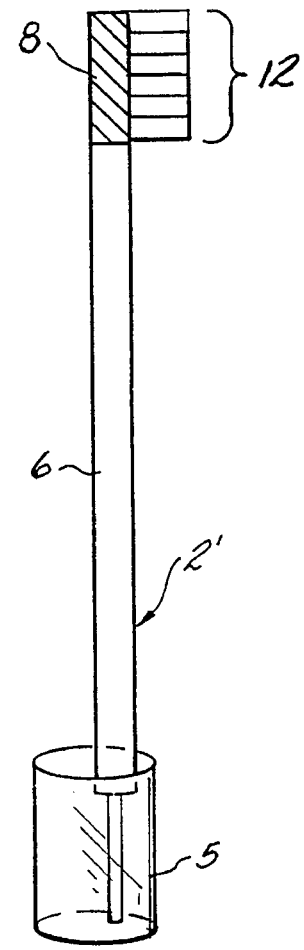
FIG. 3 is view similar to FIG. 1, but showing a second embodiment of a device which can be used to test a beverage.

Referring now to the drawings, there is shown in FIGS. 1 and 2 a dipstick denoted generally by the numeral 2, which is operable to analyze a beverage to determine its caffeine content. The dipstick 2 includes one end section 4 which is dipped into the beverage being analyzed and is operable to absorb some of the liquid from the beverage container (not shown). Adjacent to the dipping section 4 is a medial temperature moderation section 6. The temperature moderation section 6 is operable to transfer liquid absorbed by the dipping section 4 to a reagent section 8 at the end of the dipstick 2 opposite to the dipping section 4. The temperature moderation section 6, in addition to transferring liquid from the dipping section 4 to the reagent section 8, is operable to moderate the temperature of the beverage being analyzed so that an initially hot beverage such as coffee will cool off before it enters the reagent section 8; and an initially cold beverage such as cola will warm up before it enters the reagent section. In this way, the temperature of the beverage being analyzed will not adversely influence the validity of the results. Opposite sides of the temperature moderation section 6 and the reagent section 8 of the dipstick 2 are covered by a gas-permeable plastic film skin 10 which may be formed from a polyurethane polyisocyanate copolymer, or the like gas-permeable plastic. The plastic film skins 10 protect the temperature moderature section 6 from contact by the user of the dipstick 2; and the skins 10 also protect the user from contact with the reagents in the reagent section 8 of the dipstick 2. The film skins 10 are gas permeable so as to allow oxygen-dependent reactions to take place in the reagent section 8. The dipstick 2 may include a graduated color chart section 12 which includes a plurality of subcomponents 14–24. The subcomponents 14–24 are preprinted with different color hues which may be formed in the reagent section 8 of the dipstick 2. In order to determine the concentration of caffeine in the beverage being tested, the color hue found in the reagent section 8 of the dipstick 2 is compared with the color hues in the color chart components 14–24. Alternatively, the color chart could be provided as a separate component that is packaged along with the dipsticks. The device shown in FIG. 3 is a variant of the device of FIG. 1 wherein a small cup 5 is included at the end of the dipstick 2' for removing a small amount of the beverage from its container. The wicking section 6 of the device 2' extends into the interior of the cup 5.

Two examples of reagents which can be used in the reagent section 8 of the dipstick 2 to detect caffeine in a beverage are as follows:

EXAMPLE 1

The first example utilizes a xanthine oxidase enzyme reaction to produce a chromogenic change on the dipstick. The reagent section of the dipstick contains xanthine oxidase enzyme coupled with a horseradish peroxidase enzyme; a buffer (pH 7.5 phosphate buffer); and a chromogen which produces a color change on the dipstick when a coupled enzymatic reaction takes place. The xanthine oxidase is immobilized by cross linking with a reagent such as glutaraldehyde on a dipstick surface which is coated with a material such as gelatin, polyacrylamide, alginates, or the like. The reaction of $O_2$ and caffeine in the presence of the xanthine oxidase enzyme produces hydrogen peroxide ($H_2O_2$) and oxidized caffeine. The $H_2O$ formed reacts with the chromogen in the presence of the peroxidase enzyme to produce an oxidized form of the chromogen whose hue varies with the concentration of hydrogen peroxide, and thus caffeine. The calibration strip, or a separate calibration chart, with fixed colors for different concentration ranges is compared with the color produced by the beverage of unknown caffeine content in order to complete the analysis.

EXAMPLE II

The second example utilizes an apoenzyme reactivation reaction to produce a chromogenic change in the dipstick. The reagent section of the dipstick contains monoclonal antibodies reactive against caffeine; a caffeine conjugate labeled with flavin adenine dinucleotide (FAD); apoglucose oxidase which reacts with unbound caffeine conjugate; a chromogen buffer; and peroxidase. Competitive binding between caffeine and caffeine conjugate on the antibody releases more conjugate for reaction with the apoglucose enzyme thereby increasing the amount of hydrogen peroxide produced by the glucose oxidase reaction. The chromogen color will vary in hue depending on the concentration of hydrogen peroxide, and thus on caffeine concentration, as in Example I. Again, a calibration chart with fixed colors is used to complete the quantitative assay.

The color producing reaction is the same for both of the Examples. Chromogens which could be used in either Example I or Example II include potassium iodide (KI) chromogen, tetramethylbenzidine, and homovanillic acid.

Various beverages contain certain caffeine concentrations. For example, regular brewed coffee contains about 100–150 mg caffeine per 180 milliliters of beverage. Instant coffee contains about 60–80 mg caffeine per 180 milliliters of beverage. Tea contains about 40–100 mg caffeine per 180 milliliters of beverage. Cola contains about 17–55 mg caffeine per 180 milliliters of beverage. Decaffeinated or caffeine-free beverages, if as represented, should contain less than about 10 mg caffeine per 180 milliliters of beverage. It will be noted from the above, that the amount of caffeine in a beverage being tested will produce a characteristic hue in the reagent section, the intensity of which hue will be proportional to the amount of caffeine in the beverage.

It will be appreciated that the device and method of this invention can be easily used by a beverage consumer to measure the amount of caffeine in a beverage about to be consumed. The device used to perform the beverage analysis is inexpensive, may be carried about by one in a pocket or purse, and can be used to analyze both hot and cold beverages for caffeine content.

Since many changes and variations of the disclosed embodiment of the invention may be made without departing from the inventive concept, it is not intended to limit the invention otherwise that as required by the appended claims.

What is claimed is:

1. A dipstick device for detecting the concentration of caffeine in a beverage, said dipstick device comprising:
   a) a dipping section at one end of said device for dipping into and absorbing the beverage, said dipping section being constructed and adapted such that it is devoid of reagent and prevents reagent from flowing into said dipping section and beverage,
   b) a reagent section located at the opposite end of said device and in fluid communication with said dipping section, said reagent section being impregnated with a reagent which, when reacted with caffeine, is operable to produce a characteristic chromogenic change in the reagent section which varies with the concentration of caffeine in the beverage.

2. The device of claim 1 further comprising a wicking section interposed between said dipping section and said reagent section, said wicking section being operable to transfer beverage from said dipping section to said reagent section.

3. The device of claim 1 further comprising a covering of a gas-permeable plastic overlying said reagent section.

4. The device of claim 3 wherein said plastic also overlies said wicking section.

5. The device of claim 1 wherein said reagent includes an oxidase enzyme, a peroxidase enzyme, and a reactive chromogen which when oxidized in the presence of caffeine produces said characteristic chromogenic change.

6. The device of claim 1 wherein said reagent utilizes a xanthine oxidase enzyme reaction to produce said characteristic chromogenic change.

7. The device of claim 1 wherein said reagent includes antibodies reactive against caffeine, a labeled caffeine conjugate and, an oxidase enzyme which reacts with unbound caffeine conjugate to produce the characteristic chromogenic change.

8. The device of claim 1 wherein said reagent utilizes an apoenzyme reactivation reaction to produce said characteristic chromogenic change.

9. The device of claim 1 further comprising a color chart adjacent to said reagent section, said color chart having hue gradations for comparison with the characteristic color produced in the reagent section.

10. A device for detecting the concentration of caffeine in a beverage, said device comprising:

a) an absorbant material which is operable to absorb the beverage;

b) said absorbant material having s first portion thereof which is impregnated with a reagent which, when reacted with caffeine, is operable to produce a characteristic chromogenic change in the absorbant material which chromogenic change varies with the concentration of caffeine in the beverage, and having a second portion thereof which is devoid of said reagent ad which is adapted to be dipped into a beverage, said first and second portion being in fluid Communication with each other; and c) said device being constructed and adapted such that reagent is prevented from flowing from said first portion into said second portion and beverage.

11. A method for detecting the concentration of caffeine in a beverage in a container, said method comprising the steps of:

a) transferring a portion of the beverage from the container onto an absorbant material;

b) reacting said transferred portion of the beverage with a reagent in said absorbant material so as to produce a color hue in the reagent which color hue varies with the concentration of caffeine in the beverage; and c) preventing the reagent from comingling with the beverage in the container.

* * * * *